United States Patent [19]
Raspanti et al.

[11] Patent Number: 5,738,842
[45] Date of Patent: Apr. 14, 1998

[54] SUN PROTECTING COSMETIC COMPOSITIONS COMPRISING DERIVATIVES OF DIBENZOYLMETHANE, OF DIPHENYLCYANOACRYLIC ACID AND OF TRIAZINE

[75] Inventors: Giuseppe Raspanti; Alverio Malpede, both of Bergamo, Italy

[73] Assignee: 3V Inc., Weehawken, N.J.

[21] Appl. No.: 753,759

[22] Filed: Nov. 29, 1996

[51] Int. Cl.$^6$ .......................... A61K 7/42; A61K 31/53; A61K 31/275; A61K 31/12
[52] U.S. Cl. .......................... 424/59; 424/60; 424/400; 424/401; 574/245; 574/521; 574/685; 574/687; 544/197; 558/400; 568/331
[58] Field of Search ................ 424/59, 60, 400, 424/401; 514/245, 521, 685, 687; 544/197; 558/400; 568/331

[56] References Cited

U.S. PATENT DOCUMENTS 5,639,446  6/1997  Raspanti et al. .......................... 424/59

*Primary Examiner*—Shelley A. Dodson
*Attorney, Agent, or Firm*—Griffin, Butler Whisenhunt & Szipl

[57] ABSTRACT

Cosmetic compositions containing sunscreens against sun radiation ranging from 280 to 380 nm, and their use for the protection of the skin from UV radiation. The sunscreens comprise, with respect to the weight of the composition:

a) from 1 to 10% of one or more derivatives of formula (I)

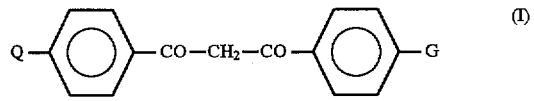

wherein Q is hydrogen or $C_1$–$C_4$ alkoxy and G is $C_1$–$C_8$ alkyl;

b) from 0.5 to 10% of one or more derivatives of formula (II):

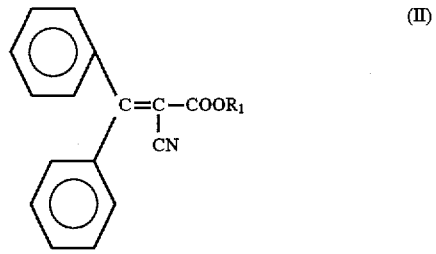

wherein $R_1$ is $C_1$–$C_8$ alkyl; and c) from 1 to 10% of one or more derivatives of formula (III)

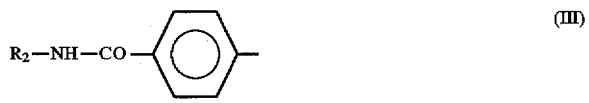

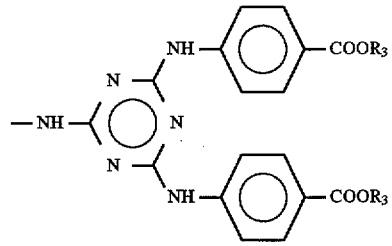

wherein R2 is $C_1$–$C_8$ alkyl and $R_3$ has independently the same meanings as $R_2$ or is hydrogen or is an alkali metal;

with the condition that the weight ratio between the compounds of formula (II) and the compounds of formula (I) is at least 0.5.

13 Claims, No Drawings

SUN PROTECTING COSMETIC COMPOSITIONS COMPRISING DERIVATIVES OF DIBENZOYLMETHANE, OF DIPHENYLCYANOACRYLIC ACID AND OF TRIAZINE

The present invention relates to cosmetic compositions, in the foregoing called sun-protecting formulations, useful for the protection of skin and/or hair from ultraviolet radiations containing photostable mixtures of sunscreens.

BACKGROUND OF THE INVENTION

It is well known that sun radiations ranging from 280 to 400 nm are noxious to human skin; in particular those radiations with a wavelength between 280 and 320 nm, the so-called UV-B radiations, cause erythema and cutaneous sunburns, whose severity depends on the duration of the exposition and on the kind of skin. It has been ascertained that also radiations ranging from 320 to 400 nm, so-called UV-A and responsible of skin tanning, can cause alterations in the skin and damages which may not be disregarded, especially in cases of sensible skins or in case of continuous exposition to radiations.

It has been demonstrated that UV-A radiation other than causing damages to elastin and collagen, whose consequence is skin ageing, can also be the cause of a number of phototoxic and photoallergic reactions. Moreover the UV-B noxious action can be enhanced by the presence of UV-A (Willis et al.: Journal of Investigative Dermatology vol. 59,416, 1972).

Some compounds derived from cinnamic acid, 4-aminobenzoic acid and benzylidencamphor are well-known and also used for the preparation of sun-protecting formulations for the protection from the UV-B radiations. These compounds, other than a more or less sufficient efficacy, do not have a satisfactory photostability 2-Ethylhexyl-cyano-$\beta,\beta'$-diphenylacrylate and 2-hydroxy-4-methoxybenzophenone show good photostability, however their absorption is very low, therefore they have negligible efficacy.

2,4,6-Trianilino(p-carbo-2-ethylhexyloxy)-1,3,5-triazine is a sunscreen described in U.S. Pat. No. 4,617,390 and recently marketed by BASF under the trade name Uvinul®T 150. This sunscreen shows a high absorption at about 310 nm, thus it has good efficacy and moreover it has a satisfactory photostability. However, due to its poor solubility in the usual cosmetic ingredients, practically the product was never successful and it is seldom used.

In the U.S. Pat. No. 5,346,691 triazine derivatives are described, having UV-B absorption at about 310 nm, which is very high. These derivatives not only have a very good photostability, but also show very good solubility in the solvents used for cosmetic formulations.

To date, on the contrary, sufficiently effective products for the protection from UV-A are not yet available, even if in the patent literature different compounds have been proposed, but their outcome is not satisfying in practical use.

At present, the UV-A sunscreens (absorber) used in practice are limited to benzophenone derivatives and to some dibenzoylmethane derivatives.

Benzophenone derivatives have a very good photostability, and can act both as UV-B filters with absorption at about 290 nm, and as UV-A filters with absorption at about 325 nm.

Nonetheless, the absorptions at two different wavelengths are relatively weak, especially in the UV-A zone at 325 nm, therefore these compounds are not able to provide a sufficient protection.

Among the derivatives of dibenzoylmethane, 4-methoxy-4'-ter-butyldibenzoylmethane and 4-isopropyldibenzoylmethane are those commercially known. These compounds show a good absorption at 360 nm and a fair solubility in the solvents usually employed in cosmetics.

However, their use is difficult, because they are not sufficiently photostable (Int. J. Cosm. Science 10, 53, 1988). Accordingly, the formulations containing these compounds can not guarantee a sufficient protection against UV-A, since the protective filter is quickly degraded by the radiation itself.

In order to avoid this quick degradation and give these UV-A filters some photostability, in the patents GB 2,198,944, WO 91/11989 and WO 94/04131 particular combinations among UV-B filters belonging to the benzylidencamphor and diphenylcyanoacrylate classes and the dibenzoylmethane derivatives are proposed.

The results, however, still cannot be considered sufficient, because, even with large amounts of the above UV-B filters, it is not possible to give the dibenzoylmethane derivatives a satisfactory photostability.

For the photoprotection of the skin a large number of sun-protecting formulations have been proposed and in this concern, a very wide patent literature exists.

Therefore, the actual problem to be solved is the stabilization of sunscreens in cosmetic formulations, in particular of dibenzoylmethane derivatives. Moreover, another actual problem is the cosmetic treatment of skin when exposed to sunlight such as to allow an agreeable tanning without incurring in sunburns.

SUMMARY OF THE INVENTION

It has now surprisingly been found that photostable sun-protecting formulations with protective activity against UV radiations ranging from 290 to 380 nm, i.e. UV-B and UV-A are obtained by means of combinations comprising, with respect to the total weight of the composition, a) from 1 to 10% of one or more compounds of formula (I)

$$Q-\underset{}{\bigcirc}-CO-CH_2-CO-\underset{}{\bigcirc}-G \quad (I)$$

wherein Q is hydrogen, straight or branched $C_1-C_4$ alkoxy group and G is straight or branched $C_1-C_8$ alkyl, b) from 0.5 to 10% of one or more compounds of formula (II)

$$\underset{}{\bigcirc}\diagdown\underset{}{\underset{}{\bigcirc}\diagup}C=\underset{CN}{\overset{}{C}}-COOR_1 \quad (II)$$

wherein $R_1$ is a straight or branched $C_1-C_8$ alkyl;

c) from 1 to 10% of one or more compounds of formula (III)

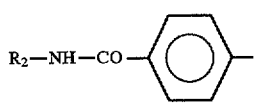
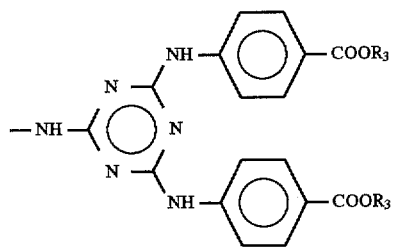

wherein $R_2$ is straight or branched $C_1$–$C_8$ alkyl;

$R_3$ has the same meanings of $R_2$ or is hydrogen or an alkali metal;

with the condition that the weight ratio between the compounds of formula (II) and those of formula (I) is at least 0.5.

Therefore, a cosmetic composition comprising in admixture with a cosmetic substrate the components a), b) and c) as described above is an object of the present invention.

Another object of the present invention is a method for the cosmetic treatment or the protection of human skin when exposed to sunlight, said method consisting in applying a suitable amount of a cosmetic composition as described above.

A further object of the present invention is a method for the stabilization of a cosmetic composition against UV radiation comprising the addition to the cosmetic substrate a photostabilizing mixture as described in the foregoing.

DETAILED DESCRIPTION OF THE INVENTION

Preferred compounds of formula (I) are those wherein Q is methoxy and G is ter-butyl, or Q is hydrogen and G is isopropyl.

Preferred compounds of formula (II) are 2-ethylhexyl α-cyano-β,β'-diphenylacrylate marketed by BASF under the trade names of Uvinul®N539.

Preferred compounds of formula (III) are those wherein $R_2$ and $R_3$ can be the same or different and are straight or branched $C_4$–$C_8$ alkyl.

By means of the combinations according to the present invention, particularly photostable sun-protecting formulations with protective action both in UV-A and UV-B are obtained. Notwithstanding the fact that the present inventors do not want to be bound to theoretical interpretations, it may be supposed that the compounds of formula (II) stabilize the UV-A filters of formula (I), which are per se not photostable.

On the other hand, absorption in UV-B range of the compounds of formula (II) is low, then their photoprotective action is very weak. It has surprisingly been found that this action is enormously enhanced by the presence of the compounds of formula (III).

The weight ratio between one or more compounds of formula (II) and one or more compounds of formula (I) must be at least 0.5.

Examples of straight or branched $C_1$–$C_8$ alkyl are methyl, ethyl, propyl, butyl, pentyl, hexyl, heptyl, octyl and their isomers, in particular isopropyl, ter-butyl, 2-ethylhexyl.

Examples of straight or branched $C_1$–$C_4$ alkoxy are methoxy, ethoxy, propoxy, butoxy, and their isomers. Examples of alkali metal are sodium, lithium and potassium.

The derivatives of the dibenzoylmethane of formula (I), are described in the patents U.S. Pat. No. 4,387,089 and U.S. Pat. No. 4,489,057. The commercial compounds are Parsol®1789, (4-methoxy-4'-ter-butyldibenzoylmethane) by Givaudan and Eusolex®8020, (4-isopropyldibenzoylmethane) by Merck. The compounds of formula (III) are described in the patent U.S. Pat. No. 5,346,691.

Very often these sun-protecting formulations are in the form of oil-in-water emulsion of kind and containing, in variable concentrations, one or more organic lipophilic and/or hydrophilic sunscreens, capable of absorbing more or less intensely UV radiations of sunlight.

The kind of sunscreens and their suitable amount are selected depending on the desired sun protecting factor (SPF). SPF is an index of protection and is expressed as the ratio between the time of irradiation necessary to reach the erythematogenic threshold in the presence of the UV filter and the time necessary to reach the erythematogenic threshold in the absence of the UV filter. SPF can be determined according to the method described by B. Diffey and J. Robson in J. Soc. Cosmet. Chem. 40, 127–133 (1989).

It is thus possible to prepare sun-protecting formulations with high SPF, suitable to guarantee a continuous protection of the skin also during prolonged expositions to sunlight, so avoiding frequent and repeated applications necessary for an effective protection.

According to the present invention, the photostable cosmetic compositions suitable to skin protection from UV radiations with wavelength between 290 and 380 nm comprise a cosmetic substrate containing, with respect to the weight of the composition, from 1 to 10% of one or more compounds of formula (I), from 0.5 to 10% of one or more compounds of formula (II) and from 1 to 10% of one or more compounds of formula (III), with the condition that the weight ratio between the compounds of formula (II) and those of formula (I) is at least 0.5.

The sun-protecting formulations according to the present invention, once applied on epidermis, exert a protecting action against the noxious effects of UV radiation, thus avoiding the formation of erythema or sunburns or an early skin ageing.

The compositions of the invention can also be useful for the treatment, then the protection, of hair or of make-up in decorative cosmetic.

According to the present invention the cosmetic formulations can be solutions, lotions, emulsions of the water-in-oil or oil-in-water type; or can also be in the form of gels, lipsticks, aerosol.

The compositions according to the present invention are prepared by formulating the ingredients usually employed, such as for example oils, fats, emulsifiers, moisturizing agents, humectants, emollients, preservatives, surfactants, thickening agents, perfumes, pigments, dyes and other else such as alcohols, polyols, electrolytes, siliconic derivatives.

The more commonly used solvents are triglycerides of caprinic or caprilic acid, castor oil, esters of fatty acids with isopropanol, propylene glycol, glycerin, propylene glycol monomethyl- or monoethyl- or monobutylether.

The cosmetic formulations according to the present invention other than UV-absorber of formula (I), (II) and (III) can also contain other complementary sunscreens active in UV-B or in UV-A, commonly used in cosmetic, such as for example: derivatives of 4-methoxycinnamic acid, derivatives of salicylic acid, derivatives of p-aminobenzoic acid, derivatives of benzylidencamphor, derivatives of 2-phenylbenzimidazole.

The sun-protecting formulations according to the present invention can also contain inorganic pigments commonly used in cosmetics; such as for example titanium dioxide, zinc oxide, silica or aluminium oxide.

The present invention comprises also the protection of the cosmetic compositions themselves from UV radiation by means of the addition of from 2 to 10% by weight with respect to the composition of a photostabilizing mixture consisting of the combination of compounds of formula (I), (II) and (III), described hereinafter. In this case it is a matter of compositions whose components can undergo unwanted light-induced degradation or colouring, as for example shampoos and hair lacquers, hair dressing lotions, hair-dyeing compositions, make-up formulations, as nail lacquers, foundation, lipstick. Preferred cosmetic formulations are the ones for the protection of skin from sun radiations. Therefore, it is another object of the present invention a photostabilizing mixture consisting of:

a) at least a compound of formula (I)

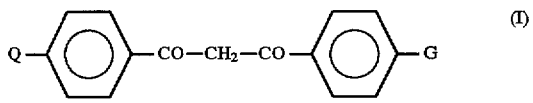

wherein Q is hydrogen, straight or branched $C_1$–$C_4$ alkoxy group and G is straight or branched $C_1$–$C_8$ alkyl, b) at least a compound of formula (II)

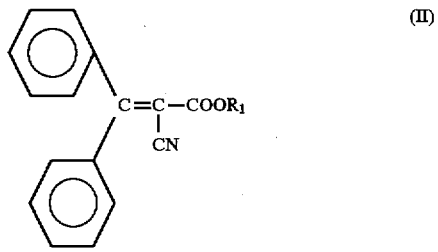

wherein $R_1$ is a straight or branched $C_1$–$C_8$ alkyl;

c) at least a compound of formula (III)

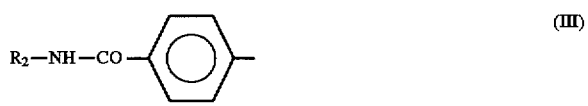

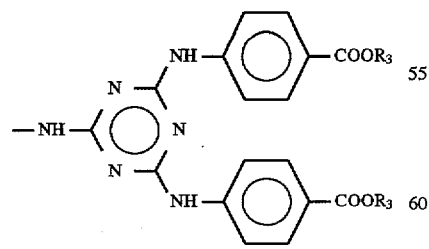

wherein $R_2$ is straight or branched $C_1$–$C_8$ alkyl;

$R_3$ has the same meanings of $R_2$ or is hydrogen or an alkali metal;

with the condition that the weight ratio between the compounds of formula (II) and those of formula (I) is at least 0.5.

The following examples further illustrate the invention.

EXAMPLE A—PHOTOSTABILITY

A solution of the sunscreens or their combinations in a solvent mixture consisting of 70% ethyl alcohol and 30% isopropyl myristate was prepared.

From each solution 2 samples of 20 microliters were withdrawn by means of a microsiringe and put on 2×5 cm microscope slides.

The samples so prepared were left in the air at room temperature for 30 minutes, as to allow ethanol evaporation. Subsequently, one of the two samples was exposed to UV irradiation for 2 and 4 hours in a Suntest Heraeus CPS+ apparatus, fitted with a Xenon lamp and a filter system in order to cut off UV radiation lower than 290 nm and IR radiation.

After exposition, the slides were washed with 50 or 100 ml of ethanol, as to quantitatively solubilize the deposed material.

In the so obtained ethanolic solutions, without further dilution, absorbance was measured in quartz cuvettes with 1 cm optical path by means of a spectrophotometer Perkin-Elmer Lambda 2.

Photostability F was calculated as the percent ratio between absorbance at the wavelength of maximum absorption of the exposed sample and the one of the not exposed sample.

For the combinations, photostability was calculated only for the filter of formula (I).

The results are shown in the following Table.

TABLE

| Sunscreens | g/100 ml solvent | F 2 hours | F 4 hours |
|---|---|---|---|
| A | 5 | 23 | 14 |
| B | 5 | 91 | 83 |
| C | 5 | 100 | 100 |
| D | 5 | 100 | 100 |
| A + B | 5 + 5 | 88 | 76 |
| A + B + C | 2 + 2 + 4 | 87 | 76 |
| A + B + D | 2 + 4 + 4 | 90 | 84 |

A = 4-methoxy-4'-ter-butyldibenzoylmethane
B = 2-ethylhexyl-α-cyano-β,β'-diphenylacrylate
C = Compound of formula III, $R_2$ = ter-butyl; $R_3$ = 2-ethylhexyl
D = Compound of formula III, $R_2$ = ter-octyl; $R_3$ = 2-ethylhexyl

EXAMPLE 1—LOTION

| | |
|---|---|
| Filter A | 2.5 g |
| Filter B | 2.5 g |
| Filter C | 2.0 g |
| Octyl octanoate | 46.0 g |
| Triglycerides $C_8$-$C_{10}$ | 34.5 g |
| Dioctylcyclohexane | 12.4 g |
| Perfume | 0.1 g |

The solvent mixture was heated to 60° C., while stirring, the three sunscreens were added, stirring was continued for 10–15 minutes, perfume was added after cooling.

EXAMPLE 2—O/W SUN CREAM

| | |
|---|---|
| $C_{12}$-$C_{15}$ Alkylbenzoate | 5.0 g |
| Diisopropyl adipate | 5.0 g |
| Karitè butter | 2.0 g |
| α-Bisabalol | 0.5 g |
| Filter A | 3.0 g |
| Filter B | 2.5 g |
| Filter C | 4.0 g |
| Stabylen 30 (R) (Thickening agent 3V SIGMA) | 0.3 g |
| Synthalen K (R) (Thickening agent 3V SIGMA) | 0.3 g |
| Abiol (R) (Preservative 3V SIGMA) | 0.3 g |
| Methylparaben | 0.2 g |
| Propylparaben | 0.1 g |
| Glycerin | 5.0 g |
| Aminomethylpropanol | 0.5 g |
| Water | up to 100.0 g |
| Perfume | q.s. |

The fatty phase was heated to 70° C., sunscreens were added and stirring was done for 10–15 minutes. Stabylen 30 and Synthalen K were dispersed in water and the fatty phase was added under strong stirring to the 70° C. previously warmed aqueous dispersion. The resulting mixture was neutralized with aminomethylpropanol, was cooled to 35° C. and preservatives, glycerin and perfume were added.

EXAMPLE 3—O/W DAY-CREAM

| | |
|---|---|
| Triglyceryl methylglucose distearate | 4.0 g |
| Glyceryl stearate | 1.0 g |
| $C_{12}$-$C_{15}$ Alkylbenzoate | 7.5 g |
| Avocado oil | 5.0 g |
| Diisopropyl adipate | 5.0 g |
| Filter A | 1.5 g |
| Filter B | 2.0 g |
| Filter D | 1.5 g |
| Synthalen K (Thickening agent 3V SIGMA) | 0.2 g |
| Abiol (R) (Preservative 3V SIGMA) | 0.3 g |
| Methylparaben | 0.2 g |
| Propylparaben | 0.1 g |
| Aminomethylpropanol | 0.15 g |
| Glycerin | 3.0 g |
| Water | up to 100.0 g |
| Perfume | q.s. |

Operations were performed as described in Example 2.

EXAMPLE 4—O/W SUN MILK

| | |
|---|---|
| PEG-7 Hydrogenated castor oil | 7.5 g |
| Alcohols of lanolin in mineral oil | 2.5 g |
| Octyl octanoate | 7.5 g |
| Dioctylcyclohexane | 5.0 g |
| Cetylstearyl octanoate | 5.0 g |
| Filter A | 3.0 g |
| Filter B | 4.0 g |
| Filter C | 3.5 g |
| Abiol (R) (Preservative 3V SIGMA) | 0.3 g |
| Glycerin | 5.0 g |
| Water | up to 100.0 g |
| Perfume | q.s. |

The fatty phase was heated to 70° C. and the sunscreens were added.

70° C. pre-heated water was added to the fatty phase under strong stirring. After cooling, preservative, glycerin and perfume were added.

EXAMPLE 5—LIPSTICK

The base mixture was first prepared:

| | |
|---|---|
| Beeswax | 13.0 g |
| Carnauba wax | 7.5 g |
| Lanolin | 5.0 g |
| Isopropyl myristate | 8.0 g |
| Mineral oil | 3.0 g |
| Castor oil | 63.5 g |

85 g of this mixture were warmed to melt. 8 g of filter A, 7 g of filter C and 9 g of filter B as well as perfume and dyes were added to the molten mass, then it was diluted to 1000 g with castor oil and it was cooled at room temperature.

We claim:

1. A cosmetic composition comprising, in admixture with a cosmetic substrate, with respect to the total weight of the composition:

a) from 1 to 10% of one or more compounds of formula (I)

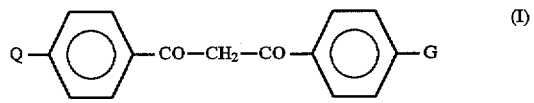

wherein Q is hydrogen, straight or branched $C_1$–$C_4$ alkoxy and G is straight or branched $C_1$–$C_8$ alkyl, b) from 0.5 to 10% of one or more compounds of formula (II)

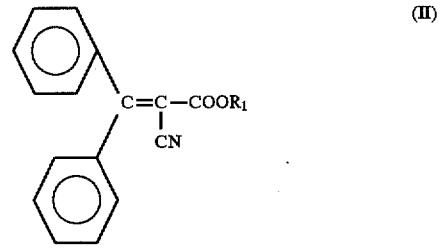

wherein $R_1$ is a straight or branched $C_1$–$C_8$ alkyl;

c) from 1 to 10% of one or more compounds of formula (III)

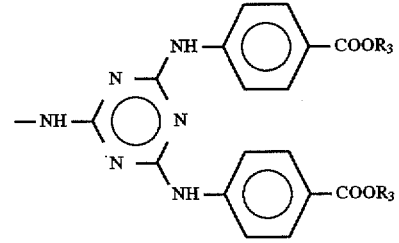

wherein $R_2$ is straight or branched $C_1$–$C_8$ alkyl;

$R_3$ has the same meanings of $R_2$ or is hydrogen or an alkali metal;

with the condition that the weight ratio between the compounds of formula (II) and those of formula (I) is at least 0.5.

2. A cosmetic composition according to claim 1, wherein in formula (I) Q is methoxy and G is ter-butyl.

3. A cosmetic composition according to claim 1, wherein in formula (I) Q is hydrogen and G is isopropyl.

4. A cosmetic composition according to claim 1, wherein in formula (II), $R_1$ is 2-ethylhexyl.

5. A cosmetic composition according to claim 1, wherein in formula (III) $R_2$ and $R_3$, that can be the same or different, are straight or branched $C_4$–$C_8$ alkyl.

6. A cosmetic composition according to claim 1, containing also zinc oxide.

7. A cosmetic composition according to claim 1, containing also titanium oxide.

8. A cosmetic composition according to claim 1, containing also other sunscreens selected from the group consisting of: 4-methoxycinnamic acid derivatives, salicylic acid derivatives, p-aminobenzoic acid derivatives, benzylydenecamphor derivatives, 2-phenylbenzimidazole derivatives.

9. A cosmetic composition according to claim 1, containing as adjuvants one or more components selected from the group consisting of thickening agents, emollients, hydrating agents, preservatives, perfume.

10. A method for the cosmetic treatment of human skin when exposed to sunlight consisting in applying a suitable amount of a cosmetic composition of claim 1.

11. A method for the protective treatment of the human skin when exposed to sunlight consisting in applying a suitable amount of a cosmetic composition of claim 1.

12. A method for the stabilization of a cosmetic composition against UV radiation comprising the addition to the cosmetic substrate from 2 to 10% by weight with respect to the composition of a combination consisting of:

a) at least one compound of formula (I)

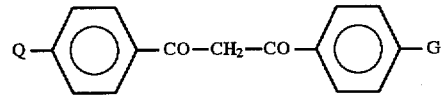

(I)

wherein Q is hydrogen, straight or branched $C_1$–$C_4$ alkoxy and G is straight or branched $C_1$–$C_8$ alkyl, b) at least one compound of formula (II)

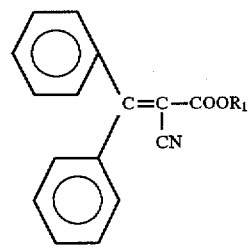

(II)

wherein $R_1$ is a straight or branched $C_1$–$C_8$ alkyl;

c) at least one compound of formula (III)

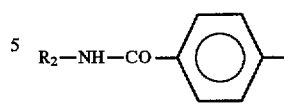

(III)

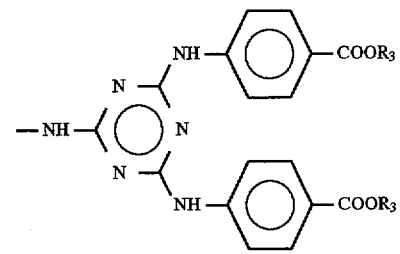

wherein $R_2$ is straight or branched $C_1$–$C_8$ alkyl;

$R_3$ has the same meanings of $R_2$ or is hydrogen or an alkali metal;

with the condition that the weight ratio between the compounds of formula (II) and those of formula (I) is at least 0.5.

13. A method for the preparation of a dermatological composition for the protection of human skin from ultraviolet radiation, said method comprising adding to a cosmetic substrate an ultraviolet-radiation-protective amount of a photostabilizing mixture consisting of:

a) at least one compound of formula (I)

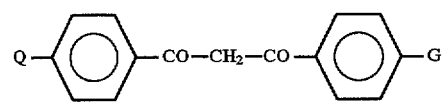

(I)

wherein Q is hydrogen or straight or branched $C_1$–$C_4$ alkoxy and G is straight or branched $C_1$–$C_8$ alkyl, b) at least one compound of formula (II)

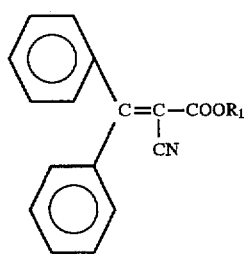

(II)

wherein $R_1$ is straight or branched $C_1$–$C_8$ alkyl; and c) at least one compound of formula (III)

(III)

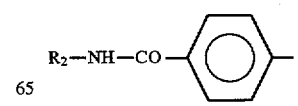

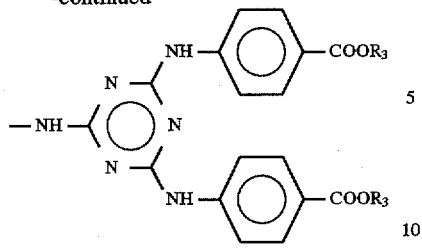
wherein $R_2$ is straight or branched $C_1$–$C_8$ alkyl and $R_3$ has the same meanings as $R_2$ or is hydrogen or an alkali metal;
with the condition that the weight ratio between the compounds of formula (II) and those of formula (I) is at least 0.5.
* * * * *